Figure 1:
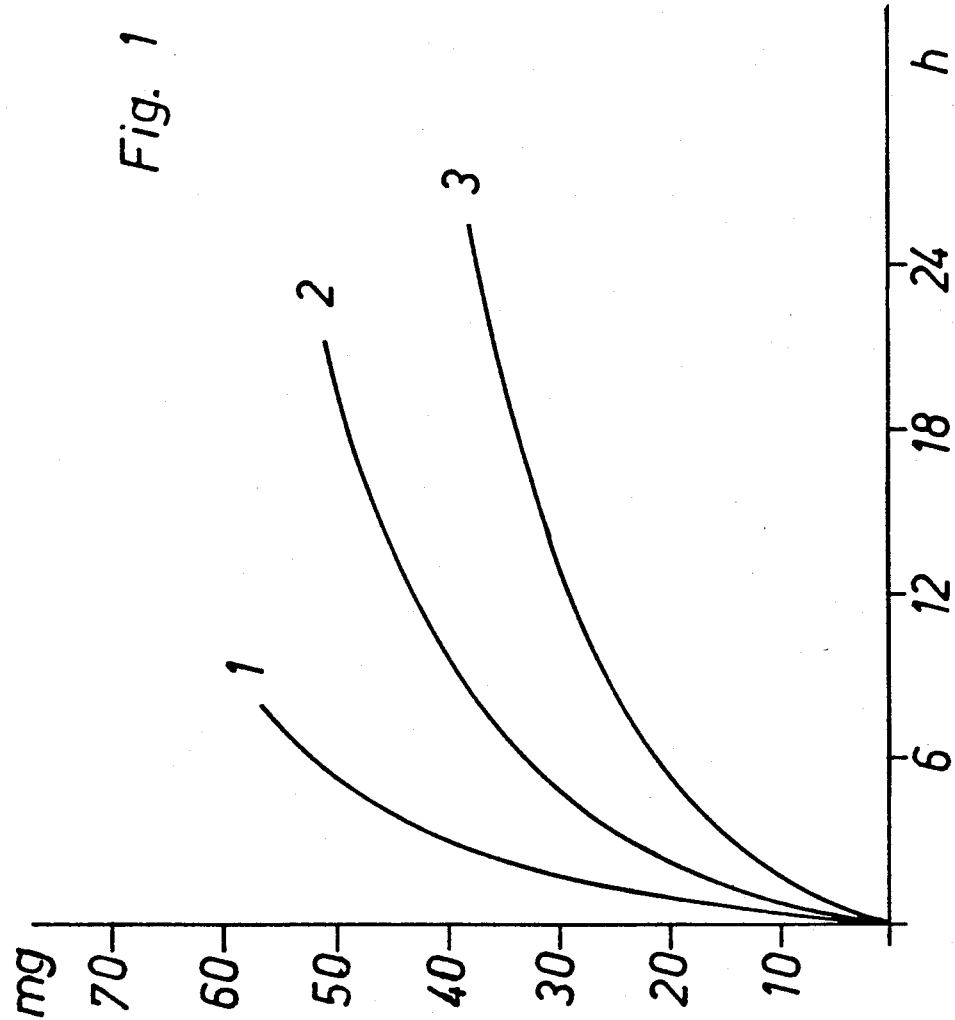

United States Patent [19]

Korsatko

[11] Patent Number: 4,491,575

[45] Date of Patent: Jan. 1, 1985

[54] COMPRESSED PRODUCTS WITH RETARDED RELEASE OF ACTIVE SUBSTANCE, A PROCESS FOR THEIR PREPARATION AND A PROCESS FOR THE LONG-TERM ADMINISTRATION OF MEDICAMENTS

[75] Inventor: Werner Korsatko, Graz, Austria

[73] Assignee: Chemie Linz Aktiengesellschaft, Linz, Austria

[21] Appl. No.: 539,720

[22] Filed: Oct. 6, 1983

[30] Foreign Application Priority Data

Oct. 15, 1982 [AT] Austria ................................ 3791/82

[51] Int. Cl.$^3$ .......................... A61K 9/22; A61K 9/26; A61K 9/32; A61K 31/74
[52] U.S. Cl. ...................................... 424/19; 424/20; 424/21; 424/22; 424/78
[58] Field of Search .................... 424/19–22, 424/78

[56] References Cited

U.S. PATENT DOCUMENTS

| | | | |
|---|---|---|---|
| 3,773,919 | 11/1973 | Boswell et al. | 424/22 |
| 3,887,699 | 6/1975 | Yolles | 424/22 |
| 3,976,071 | 8/1976 | Sadek | 424/19 |
| 3,991,766 | 11/1976 | Schmitt et al. | 424/22 |
| 4,118,470 | 10/1978 | Casey et al. | 424/19 |
| 4,293,539 | 10/1981 | Ludwig et al. | 424/19 |
| 4,328,204 | 5/1982 | Wasserman et al. | 424/19 |
| 4,331,652 | 5/1982 | Ludwig et al. | 424/19 |
| 4,333,919 | 6/1982 | Kleber et al. | 424/19 |
| 4,351,337 | 9/1982 | Sidman | 424/22 |
| 4,419,340 | 12/1983 | Yolles | 424/19 |

FOREIGN PATENT DOCUMENTS

| | | | |
|---|---|---|---|
| 2836044 | 3/1979 | Fed. Rep. of Germany . | |
| WO/0000011 | 12/1978 | PCT Int'l Appl. | 424/19 |
| 1351409 | 5/1974 | United Kingdom . | |
| 2077103A | 12/1981 | United Kingdom | 424/22 |

OTHER PUBLICATIONS

Korsatko, W. et al., Chem. Abstr. 99 #43465s (1983) of Pharm. Ind. (1983) 45: 525–527 I.
Korsatko, W. et al., Chem. Abstr. 100 #12557h (1984) of Pharm. Ind. (1983) 45(10): 1004–1007 II.
Tanaka et al., Chem. Abstr. 87 #65110b (1977) (I).
Tanaka et al., Chem. Abstr. 87 #65111c (1977) (II).
Araki et al., Chem. Abstr. 91 #57901c (1979).

*Primary Examiner*—Shep K. Rose
*Attorney, Agent, or Firm*—Mark Dryer

[57] ABSTRACT

Pharmaceutical composition for long-term oral or parenteral administration and adapted to slowly release the pharmaceutically active substance, comprising a therapeutically-active amount of a pharmaceutically-active substance homogeneously mixed with at least 20% by weight of poly-D(-)-3-hydroxybutyric acid relative to the amount of active substance; a process for preparing such composition in compressed form and a process for the long-term administration of such composition.

13 Claims, 5 Drawing Figures

COMPRESSED PRODUCTS WITH RETARDED RELEASE OF ACTIVE SUBSTANCE, A PROCESS FOR THEIR PREPARATION AND A PROCESS FOR THE LONG-TERM ADMINISTRATION OF MEDICAMENTS

The present invention relates to compressed products with retarded release of active substance for the long-term oral and parenteral administration of medicaments, a process for their preparation and a process for the controlled long-term administration of medicaments to humans and animals.

It has been known for a considerable period that drug formulations which, after a single administration, guarantee a long-lasting and continuous emission of the active substance have significant advantages for clinical practice. For this reason, therapeutic drug formulations with retarded release of active substance have been developed for a large number of pharmacologically important substances for oral and parenteral administration (cf. in this context Remington's Pharmaceutical Sciences, published by the Mack Publishing Company, Easton, Pa., U.S.A., 1975, pages 1618 to 1643) but also for topical application (for example British Patent Specification No. 1,351,409).

A known method for the preparation of retard products comprises embedding the active substance in an indigestible or insoluble support (the matrix) and then processing it to give drug formulations. Indigestible, acid-insoluble macromolecules, for example cellulose derivatives or artificial materials, such as polyvinyl chloride, polyvinyl acetate, polyethylene or polymethacrylate, are usually used as the support materials or auxiliaries. These support materials do indeed ensure a long-lasting and continuous release of the active substance and can be compressed with relative ease, but they have the disadvantage that they are not biologically degradable. This gives rise, on the one hand, on oral administration of the retard product to undesired stress on the gastrointestinal tract and, on the other hand, for example when using implants, the support which remains in the body after release of the active substance and which is not biologically degradable must be removed by surgical operation. Thus, there has been no lack of attempts to use biologically degradable polymers as the auxiliary or as the vehicle for the medicament in the preparation of depot drug formulations.

Drug formulations with retarded release of active substance, in which the matrix consists of polylactic acid in the racemic or optically active form, of polyglycolic acid or of copolymers of the two acids (polylactides), are disclosed in U.S. Pat. No. 3,773,919. After administration of these products, the vehicle is hydrolytically cleaved under physiological conditions and thus releases the active substance so that the matrix is biologically degraded after completion of the release of active substance. Formulations using polylactides show a good retard effect lasting from some weeks up to one year when the product is, for example, implanted in the body of the patient.

A disadvantage of using these biologically degradable polymers consists of the great difficulty and technical elaboration of producing the drug formultions. Because of the difficulty of mixing, the high electrostatic charge and the poor flow properties and high elasticity of the polylactides it is hardly possible, or is only possible with great technical elaboration, such as working under liquid nitrogen, to prepare homogeneous mixtures with medicaments and to compress them directly. Products which are prepared in this manner are inhomogeneous and do not give rise to satisfactory results in the release of active substance. Thus the production of drug formulations using polylactides as the retarding additive is principally restricted to the preparation of films using a fusion-compression process or to the preparation of microcapsules or microbeads by spray-drying or phase separation. However, only medicaments which are stable to heat are suitable for a fusion-compression process, and the use of organic solvents for spray-drying or phase-separation demands, for reasons of health and protection of the environment, substantial protective devices in industry, so that these two processes are used only reluctantly.

Finally, a process for the preparation of microbeads having a polymeric outer layer by phase separation is described in German Offenlegungsschrift No. 2,836,044, and it is also mentioned there that the polymer can be, in addition to other polymers, a polyhydroxybutyric acid which is not defined in more detail. However, details are only provided of the preparation of microbeads from polylactic acid, and the publication mentioned does not contain a single example of the use of polyhydroxybutyric acid.

It has now been found, surprisingly, that the advantage offered by biologically degradable and homogeneous matrix formulations can be combined with simple methods of producing drug formulations by using poly-D(-)-3-hydroxybutyric acid as the polymeric vehicle.

Accordingly, the present invention relates to compressed products with retarded release of active substance for long-term oral and parenteral administration of medicaments, containing a homogeneous mixture of a pharmaceutically active substance in a therapeutically effective amount with at least 20% by weight of poly-D(-)-3-hydroxybutyric acid, relative to the amount of active substance.

Particularly suitable drug formulations for the compressed products according to the invention are tablets of every size and shape and the cores of coated tablets. However, of course, other drug formulations are also suitable, for example very small compressed products which are subsequently filled into capsules, or multilayer tablets or coated tablets in which, in addition to the retard layer, active substances which are not retarded are to be included in another layer.

The chemical structure of poly-D(-)-3-hydroxybutyric acid is that of a linear polymer, it being possible to have 500 to 25,000 repeating units. Polymers having a molecular weight of 25,000 to 1,000,000 are particularly suitable for the preparation of the matrix formulations according to the invention. The amount of poly-D(-)-3-hydroxybutyric acid necessary for preparing the compressed products is determined by the desired rate of release of the active substance and is, for achieving a good retard effect, at least 20% by weight relative to the amount of active substance, but is not subject to any other restriction. The retard effect is dependent to a great extent on the amount of poly-D(-)-3-hydroxybutyric acid which is added, so that the rate of release of the active substance can be adjusted, virtually as required, in the period from several hours up to several months (cf. in this context, FIGS. 1 to 3).

Matrix formulations having a high content of active substance and a low content of poly-D(-)-3-hydroxybutyric acid, which can, depending on the nature of the active substance and the desired rate of release, be, for example, 20 to 40% by weight relative to the amount of active substance, are particularly suitable as retard products for oral administration. In contrast, matrix formulations having a low content of active substance and a high content of poly-D(-)-3-hydroxybutyric acid, for example from 60 to more than 95% by weight relative to the amount of active substance, are recommended for parenteral administration, for example as implants, using which the active substance is intended to be released at a constant rate, after implantation in the body, simultaneously with the biological degradation of the vehicle according to the invention over a period lasting from one week up to several months.

The poly-D(-)-3-hydroxybutyric acid required for the purpose according to the invention can be obtained relatively straightforwardly, even in large amounts, for example by using the biological process of Lafferty et al., Chem. Rundschau 30 (41) 14 to 16, 1977.

The invention also relates to a process for the preparation of these compressed products with retarded release of active substance.

Entirely in contrast to the polylactides, the poly-D(-)-3-hydroxybutyric acid shows, on the one hand, properties of low elasticity and a low tendency to electrostatic charging and, on the other hand, has good lubricant and release properties. Thus, it is possible to mix the active substance, in a simple manner, with the vehicle according to the invention and to convert the mixture into a homogeneous formulation. Homogenisation of small amounts can be carried out with a mortar and pestle or with a powder mixer. Large batches can be homogenised using rotating drums, paddle mixers, plate mixers, screw mixers, ribbon mixers, cone mixers, double-cone mixers and twin shell blenders.

It is possible, directly and without further treatment and without further additives, to compress the homogenates obtained in this manner to give tablets, cores for coated tablets or other compressed products of any desired shape. When the difficulties occurring in the production of drug formulations using the biologically degradable matrix formulations hitherto known are taken into account, it is surprising to the expert that it is possible, using the matrix system according to the invention, to prepare, simply by mixing and compressing, solid drug formulations with rates of release which can be changed almost at will.

Obviously, the homogenates of the active substance and poly-D(-)-3-hydroxybutyric acid obtainable according to the invention can also be processed by one of the customary granulation processes before compression to give granules or, if desired, the auxiliaries and additives customary in the techniques of formulation can be added.

The compressed products can be prepared using all conventional manual or automatic presses, it being possible to omit the addition of lubricants or release agents because of the good lubricant and release properties of poly-D(-)-3-hydroxybutyric acid.

It is possible to vary the compression force over the range from 1 to about 20 tonnes at will. The rate of release of the active substance shows no significant dependence on the compression force on varying the compression force in the range from 1 to 10 tonnes (cf. in this context FIG. 5).

The invention also relates to a process for the controlled long-term administration of medicaments to humans and animals using the compressed products prepared according to the invention.

In the body, poly-D(-)-3-hydroxybutyric acid is subject to biological degradation either by hydrolysis or by enzymatic routes. The active substance is entirely released over a long period from the matrix formulation according to the invention at a constant rate and with complete biological degradation of the matrix, partly by erosion of the surface and partly by diffusion processes.

Thus, release of the active substance at a constant rate for more than 20 weeks has been recorded in investigations into the release of active substance in vivo, in which compressed products prepared according to the invention, with theophylline as the active substance, were implanted subcutaneously in the neck crease of mice.

Figure 4:
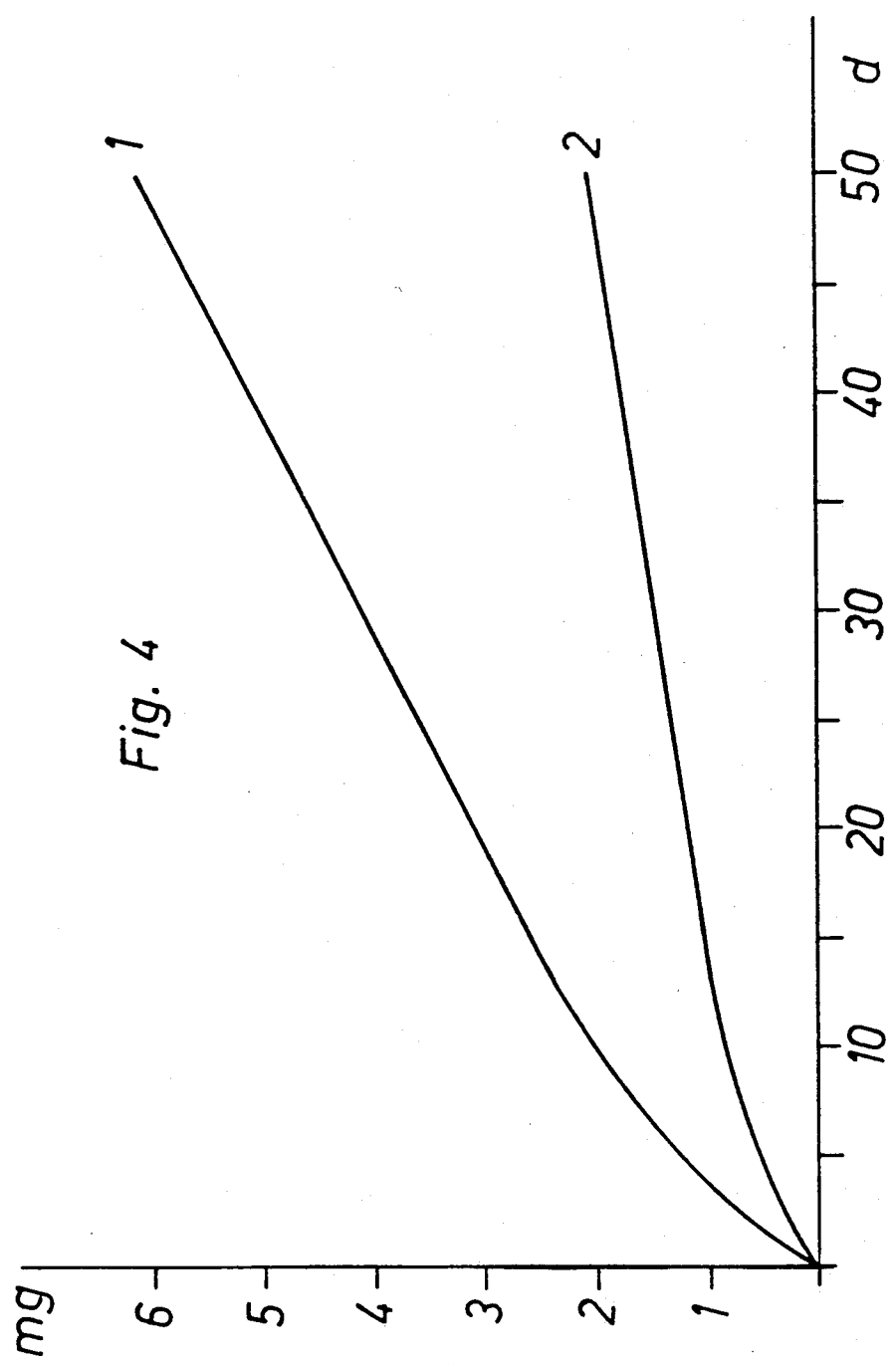
Figure 5:
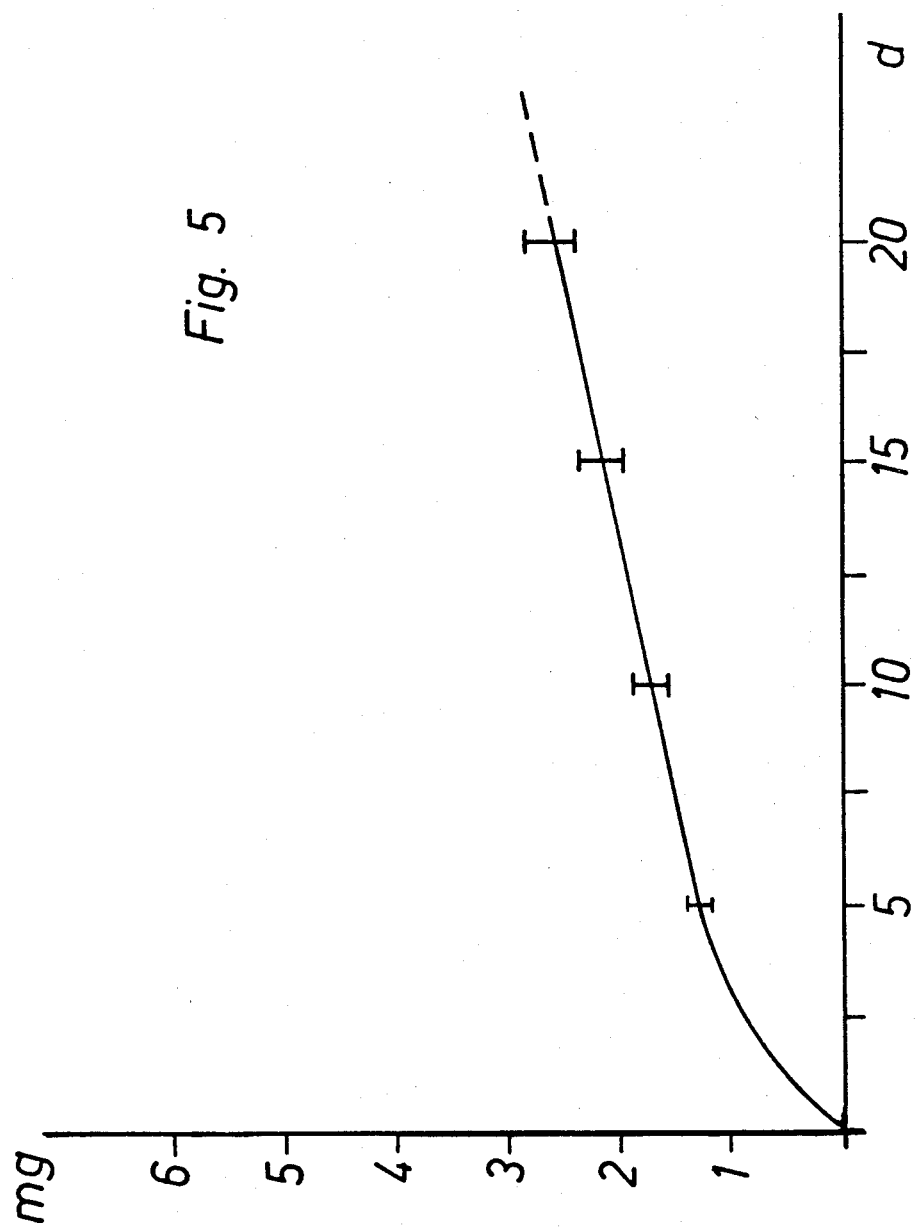

The rate of release can be modified in a variety of ways by the ratio of the amount of active substance to the matrix (Examples 1-9, FIGS. 1 to 3) by the tablet size (Examples 10 and 11, FIG. 4) and, to a slight extent, by the compression force with which the compressed products are prepared (Example 12, FIG. 5). These effects can be demonstrated in vitro in a very simple manner using a model of release under physiological conditions.

In vitro rates of release of theophylline:

In this model experiment to investigate the rate of release in vitro of theophylline, the tablets are shaken according to the physiological conditions in 100 ml of 0.9% sodium chloride solution in closed brown glass bottles of volume 200 ml at 37° C. The analytical evaluation is spectrophotometric measurement at 273 nm either directly or after dilution.

The process according to the invention is illustrated by means of the examples which follow.

EXAMPLE 1

| Formulation: | 1 tablet | Amount required for 30,000 tablets |
|---|---|---|
| 7-hydroxyethyltheophylline | 56 mg | 1.68 kg |
| poly-D(—)-3-hydroxybutyric acid of molecular weight about 100,000 | 14 mg | 0.42 kg |

Processing:

The components are screened, mixed and homogenised in a cone mixer.

The homogenate is compressed to form tablets under a compression of force of 10 tonnes, corresponding to 12.72 N/mm$^2$.

| | |
|---|---|
| tablet weight: | 70 mg |
| content of active substance: | 80% by weight (56 mg) |
| diameter: | 6.0 mm |
| thickness: | 2.0 mm |
| fracture strength: | 64 N (determined using a Schleuninger Mod. 2E/205) |

Tablets having the following contents of 7-hydroxyethyltheophylline active substance were prepared under the same processing conditions as given above:

EXAMPLE 2

Content of active substance 70% by weight (49 mg)
Matrix 30% by weight

EXAMPLE 3

Content of active substance 60% by weight (42 mg)
Matrix 40% by weight

EXAMPLE 4

Content of active substance 50% by weight (35 mg)
Matrix 50% by weight

EXAMPLE 5

Content of active substance 40% by weight (28 mg)
Matrix 50% by weight

EXAMPLE 6

Content of active substance 30% by weight (21 mg)
Matrix 70% by weight

EXAMPLE 7

Content of active substance 20% by weight (14 mg)
Matrix 80% by weight

EXAMPLE 8

Content of active substance 10% by weight (7 mg)
Matrix 90% by weight

EXAMPLE 9

Content of active substance 5% by weight (3.5 mg)
Matrix 95% by weight

Figure 2:
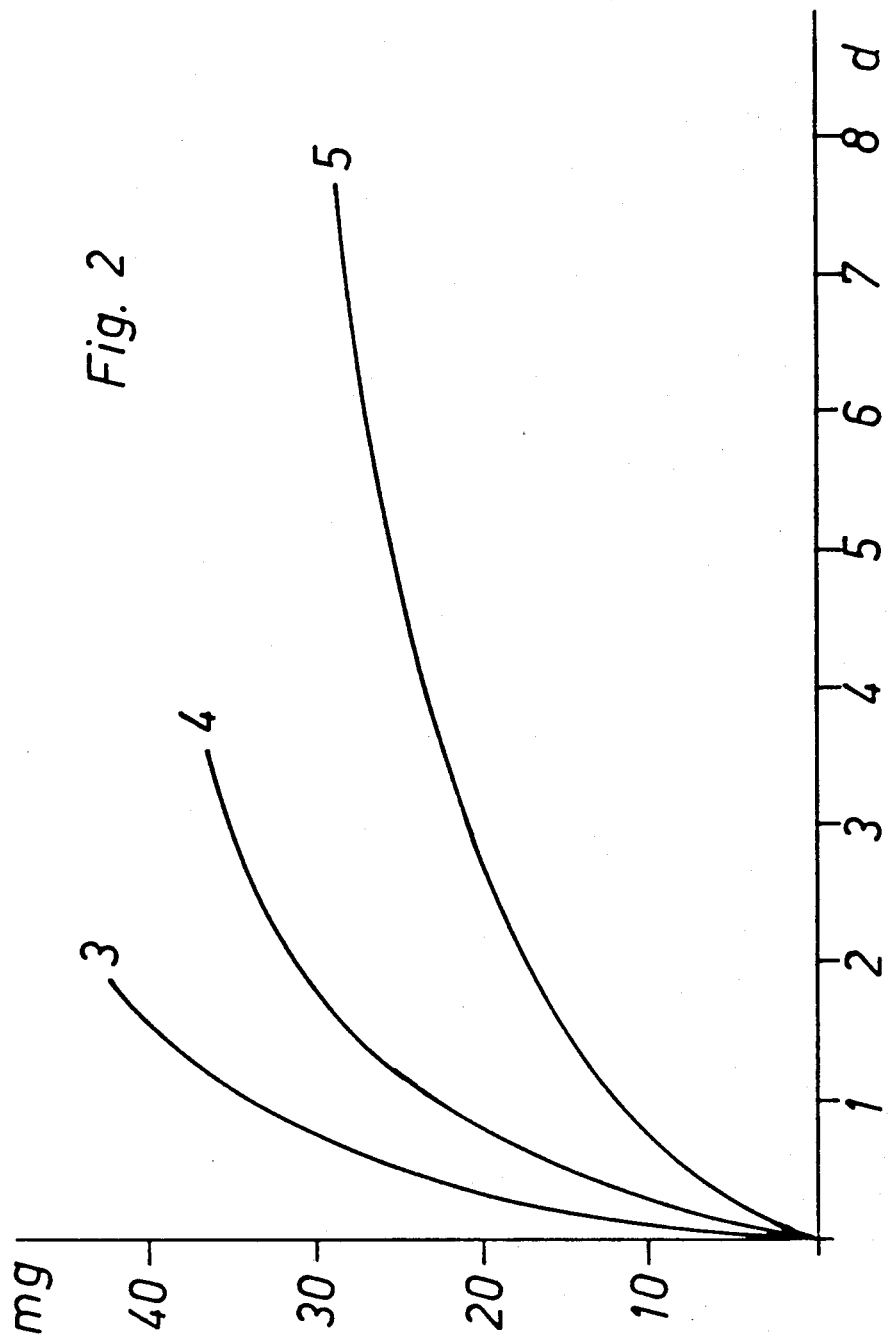
Figure 3:
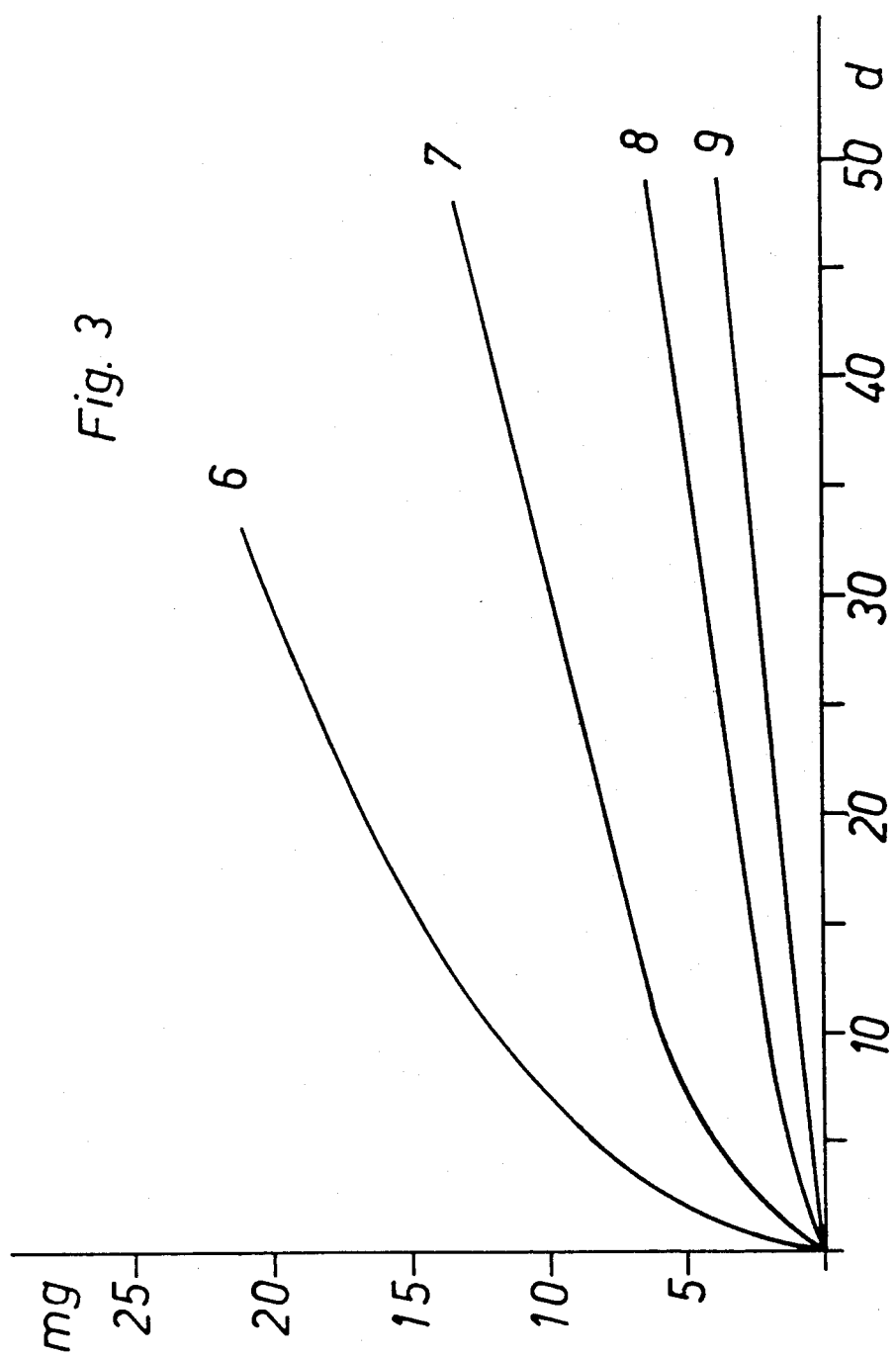

The liberation curves for Examples 1 to 9 are shown in FIGS. 1 to 3, the numbers on the liberation curves relating to Examples 1 to 9.

The fracture strength of the tablets reaches a figure of 64N at a content of active substance of 80%, and a figure of 82N at a content of active substance of 5%.

EXAMPLE 10

| Formulation: | 1 tablet | Amount required for 10,000 tablets |
|---|---|---|
| 7-hydroxyethyltheophylline | 7 mg | 70 g |
| poly-D(−)-3-hydroxybutyric acid | 63 mg | 630 g |

The constituents are homogenised as in Example 1, and the homogenate is compressed to form tablets under a compression force of 10 tonnes (12.72 N/mm$^2$).

| tablet weight: | 70 mg |
|---|---|
| content of active substance: | 10% (7 mg) |
| diameter: | 6.0 mm |
| thickness: | 2.0 mm |

The liberation curve is shown in FIG. 4, number 1.

EXAMPLE 11

| Formulation: | 1 tablet | Amount required for 10,000 tablets |
|---|---|---|
| 7-hydroxyethyltheophylline | 9 mg | 90 g |
| poly-D(−)-3-hydroxybutyric acid | 81 mg | 810 g |

The constituents are homogenised as in Example 1, and the homogenate is compressed to form tablets under a compression force of 10 tonnes (12.72 N/mm$^2$).

| tablet weight: | 90 mg |
|---|---|
| content of active substance: | 10% (9 mg) |
| diameter: | 8.0 mm |
| thickness: | 2.0 mm |

The liberation curve is shown in FIG. 4, number 2.

EXAMPLE 12

| Formulation: | 1 tablet | Amount required for 10,000 tablets |
|---|---|---|
| 7-hydroxyethyltheophylline | 7 mg | 70 g |
| poly-D(−)-3-hydroxybutyric acid | 63 mg | 630 g |

The constituents are homogenised as in Example 1, and the homogenate is compressed under a compression force of 2 tonnes (mark above the liberation curve in FIG. 5), 4, 6, 8 and 10 tonnes (mark below the liberation curve in FIG. 5). The rates of release show little dependence on the compression force in the range from 2 to 10 tonnes and are within the range indicated by the vertical marks on the liberation curve shown in FIG. 5.

What I claim is:

1. Compressed products with retarded release of active substance for long-term oral or parenteral administration of medicaments, containing a homogeneous mixture of a pharmaceutically active substance in a therapeutically effective amount with at least 20% by weight of poly-D(-)-3-hydroxybutyric acid relative to the amount of active substance.

2. Compressed products according to claim 1 in which the poly-D(-)-3-hydroxybutyric acid has a molecular weight of from 25,000 to 1,000,000.

3. Compressed products according to claim 1, suitable for long-term oral administration of medicaments, containing a homogeneous mixture of the pharmaceutically active substance with 20 to 40% by weight of poly-D(-)-3-hydroxybutyric acid relative to the amount of active substance.

4. Compressed products according to claim 1 suitable for long-term parenteral administration of medicaments, containing a homogeneous mixture of the pharmaceutically active substance with 60 to 95% by weight of poly-D(-)-3-hydroxybutyric acid relative to the amount of active substance.

5. Compressed products according to claim 1 in which the homogeneous mixture contains auxiliaries and additives customary in the techniques of formulation.

6. Process for the preparation of compressed products with retarded release of active substance for long-term oral or parenteral administration of medicaments by mixing and then homogenising a pharmaceutically active substance in a therapeutically effective amount with at least 20% by weight of poly-D(-)-3-hydroxybutyric acid relative to the amount of active substance, and compressing the homogenised mixture to form compressed products under a pressure of 1 to 20 tonnes.

7. Process according to claim 6 in which the homogenised mixture is compressed to form tablets.

8. Process according to claim 6 in which the homogenised mixture is compressed to form cores of coated tablets.

9. Process according to claim 6 in which the pharmaceutically active substance in a therapeutically effective amount is mixed with 60 to 95% by weight of poly-D(-)-3-hydroxybutyric acid relative to the amount of active substance, and the mixture is homogenised and compressed to form implants for parenteral administration.

10. Process according to claim 6 in which the pharmaceutically active substance in a therapeutically effective amount is mixed with 20 to 40% by weight of poly-D(-)-3-hydroxybutyric acid relative to the amount of active substance, and the mixture is homogenised and compressed to form tablets for oral administration.

11. Process for the controlled long-term administration of medicaments to humans and animals, comprising the administration of compressed products which contain a pharmaceutically active substance in the therapeutically effective amount required for the period of treatment in a homogeneous mixture with at least 20% by weight of poly-D(-)-3-hydroxybutyric acid relative to the amount of active substance.

12. Process according to claim 11 in which the compressed product used is a tablet which is administered orally.

13. Process according to claim 11 for the single, controlled long-term administration of medicaments, comprising the subcutaneous implantation of a compressed product for the treatment of humans or animals over several weeks, which compressed product contains the therapeutically effective amount of the medicament required for the period of treatment and contains at least 60% by weight of poly-D(-)-3-hydroxybutyric acid, the content of poly-D(-)-3-hydroxybutyric acid in the compressed product being selected such that the desired dose of the active substance is released within one day.

* * * * *